US010369126B2

(12) United States Patent
Cowieson et al.

(10) Patent No.: US 10,369,126 B2
(45) Date of Patent: Aug. 6, 2019

(54) ANIMAL FEEDS AND FEED PREMIXES CONTAINING BETAINE HYDROCHLORIDE AND A PHYTASE

(71) Applicant: RURAL CHEMICAL INDUSTRIES (AUST) PTY LTD, New South Wales (AU)

(72) Inventors: Aaron Joell Cowieson, New South Wales (AU); Peter Henry Selle, New South Wales (AU); Brett Ruth, New South Wales (AU)

(73) Assignee: Rural Chemical Industries (Aust) Pty Ltd, Mascot (AU)

( * ) Notice: Subject to any disclaimer, the term of this patent is extended or adjusted under 35 U.S.C. 154(b) by 0 days.

(21) Appl. No.: 14/894,176

(22) PCT Filed: May 29, 2014

(86) PCT No.: PCT/AU2014/050052
§ 371 (c)(1),
(2) Date: Nov. 25, 2015

(87) PCT Pub. No.: WO2014/190393
PCT Pub. Date: Dec. 4, 2014

(65) Prior Publication Data
US 2016/0106123 A1     Apr. 21, 2016

(30) Foreign Application Priority Data

May 29, 2013   (AU) ................................ 2013901954

(51) Int. Cl.
| | |
|---|---|
| *A61K 31/205* | (2006.01) |
| *A61K 38/46* | (2006.01) |
| *A61K 45/06* | (2006.01) |
| *A23K 20/105* | (2016.01) |
| *A23K 20/147* | (2016.01) |
| *A23K 20/158* | (2016.01) |
| *A23K 20/163* | (2016.01) |
| *A23K 20/189* | (2016.01) |
| *A23K 50/75* | (2016.01) |

(52) U.S. Cl.
CPC .......... *A61K 31/205* (2013.01); *A23K 20/105* (2016.05); *A23K 20/147* (2016.05); *A23K 20/158* (2016.05); *A23K 20/163* (2016.05); *A23K 20/189* (2016.05); *A23K 50/75* (2016.05); *A61K 38/465* (2013.01); *A61K 45/06* (2013.01); *C12Y 301/00* (2013.01)

(58) Field of Classification Search
CPC ....................................................... A61K 38/46
See application file for complete search history.

(56) References Cited

U.S. PATENT DOCUMENTS

2010/0068335 A1\*   3/2010  Lei ........................... C12N 9/16
                                                                          426/2

FOREIGN PATENT DOCUMENTS

| CN | 101380056 A | \* | 3/2009 |
|---|---|---|---|
| CN | 101912065 A | \* | 12/2010 |
| CN | 102640880 | | 8/2012 |
| CN | 103053831 | | 4/2013 |

OTHER PUBLICATIONS

International Search Report and Written Opinion for Application No. PCT/AU2014/050052 dated Jul. 1, 2014 (10 pages).
Selle et al., "Total and phytate-phosphorus contents and phytase activity of Australian-sourced feed ingredients for pigs and poultry" Australian Journal of Experimental Agriculture, 2003, 45:475-479.
Cowieson et al. "Supplementation of Corn-Soy-Based Diets with an *Eschericia coli*-Derived Phytase: Effects on Broiler Chick Performance and the Digestibility of Amino Acids and Metabolizability of Minerals and Energy", Poultry Science, 2006, vol. 85, No. 8, pp. 1389-1397.
Eklund et al. "Potential nutritional and physiological functions of betaine in livestock", Nutrition Research Reviews, 2005, vol. 18, No. 01, p. 31.
Garcia Neto et al. "Influence of Dietary Protein Level on the Broiler Chicken's Response to Methionine and Betaine Supplements Introduction", Poultry Science, 2000, pp. 1478-1484.
Ravindran et al. "Microbial Phytase Improves Performance, Apparent Metabolizable Energy, and Ileal Amino Acid Digestibility of Broilers Fed a Lysine-Deficient Diet", Poultry Science, 2001, vol. 80, No. 3, pp. 338-344.

\* cited by examiner

*Primary Examiner* — Ruth A Davis
(74) *Attorney, Agent, or Firm* — Fitch Even Tabin & Flannery LLP

(57) ABSTRACT

The invention relates to animal feeds and feed premixes containing synergistically effective amounts of betaine hydrochloride and a phytase.

9 Claims, No Drawings

US 10,369,126 B2

ANIMAL FEEDS AND FEED PREMIXES CONTAINING BETAINE HYDROCHLORIDE AND A PHYTASE

CROSS-REFERENCE TO RELATED APPLICATION(S)

This is a U.S. national stage entry of International Patent Application No. PCT/AU2014/050052, filed on May 29, 2014, which claims priority to Australian Patent Application No. 2013901954, filed on May 29, 2013, the entire contents of all of which are fully incorporated herein by reference.

FIELD OF THE INVENTION

The invention relates to formulation of animal feed, and to assessment of nutrient utilisation and growth performance, especially with regard to monogastric animals and livestock, including poultry.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Monogastric animal diets generally include nutrients for the growth, reproduction and health of an animal. These nutrients may take the form of proteins and amino acids, carbohydrates, fats, minerals and vitamins. "Macronutrients" are generally understood as meaning those components of a diet that provide the bulk of energy and protein for metabolism. These components are generally proteins, carbohydrates, fats and oils and fibre. "Micronutrients" generally provide the necessary cofactors for metabolism to occur. These components are generally minerals, vitamins, and amino acids. As an example, poultry diets are composed primarily of a mixture of several feedstuffs that contain macro-nutritive components, examples of which include cereal grains, soybean meal, animal by products (such as blood and bone), fats and micro-nutritive components, including mineral and vitamin premixes. Another micro-nutritive component, anhydrous betaine has also been used as a source of methyl groups.

Other non nutritive components may be added to an animal diet for a variety of purposes. Examples include pigment (such as xanthophyll), growth factors, anti-microbial agents and enzymes. One enzyme having increasing usage is phytase. Phytase is used, particularly in pork and poultry farming as a feed additive for the purpose of releasing phosphate that is bound to dietary phytate. Some of these non nutritive components may assist in the growth performance improvements and efficiency of feed utilisation.

In some countries, non-nutritive components may be combined and sold as a pre-mix formulation to a stock feed producer, who then mixes the pre-mix with nutritive components (for example grain), thereby forming a finished animal feed product that is sold to a farmer or animal producer. Alternatively, the pre-mix formulation may be sold directly to a farmer or animal producer who will then mix the pre-mix with nutritive components to form an animal feed for feeding to his stock. Sometimes these pre-mix formulations may be referred to as "feed concentrates" or "feed additive mixes."

The nutritive and non-nutritive components of animal feeds are a significant input cost in the farming of monogastric animals. As an example, the prices in the poultry meat market are currently high due to high prices for feed grains.

One problem is that a reduction in nutritive components, which might minimise costs of one or more nutritive inputs, in the absence of appropriate adjustments to an animal diet, can deleteriously impact on growth performance. Further, while adjustments that reduce the amount of nutrient components might be overcome by provision of non nutritive components that improve efficiency of feed utilisation, these non nutritive components may simply represent another input cost.

There is a need to adapt animal feed so as to minimise higher input costs, including input costs relating to nutritive and/or non nutritive components, as this would increase profitability of livestock production.

SUMMARY OF THE INVENTION

The invention seeks to address the above identified need, and/or to provide improvements in animal feeds, and in one embodiment provides an animal feed including:
  a nutrient component including one or more of a carbohydrate, fat and protein;
  a phytase;
  betaine hydrochloride (herein BHCl);
  wherein BHCl and phytase are provided in a ratio of amounts of BHCl:phytase so that the apparent metabolisable energy (AME) value of the animal feed equals the AME value of the nutrient component in the presence of the amounts of BHCl and phytase.

In another embodiment there is provided a process for producing an animal feed including the step of:
  combining a nutrient component including one or more of a carbohydrate, fat and protein with a phytase and BHCl,
  wherein the BHCl and phytase are provided in a ratio of amounts of BHCl:phytase so that the AME value of the animal feed equals the AME value of the nutrient component in the presence of the amounts of BHCl and phytase;
  thereby producing the animal feed.

In another embodiment there is provided a process for increasing the AME value of an animal feed including the steps of:
  providing an animal feed in the form of a nutrient component including one or more of carbohydrate, fat and protein, and a phytase;
  combining the animal feed with BHCl;
  wherein the BHCl is provided in a ratio of amounts of BHCl phytase so that the AME value of the animal feed equals the AME value of the nutrient component in the presence of the amounts of BHCl and phytase.

In another embodiment there is provided an animal feed premix, said premix consisting of:
  a non-nutrient component;
    wherein the non-nutrient component includes BHCl and phytase.

In another embodiment there is provided an animal feed premix, said premix consisting of:
  a non-nutrient component;
  a micronutrient component;

wherein the non-nutrient component includes BHCl and phytase.

In another embodiment there is provided a process for producing an animal feed including the step of:
combining a nutrient component including one or more of a carbohydrate, fat and protein with an animal feed premix described above.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

As described herein, the inventors have found a synergistic response in energy utilisation arising from the combination of betaine hydrochloride (BHCl) with an animal feed including a phytase. The inventors have also found that the improved energy utilisation translates to an improved growth performance.

In more detail, the inventors have found that the amount of metabolisable energy in an animal feed can be increased by providing synergistically effective amounts of BHCl and phytase to an animal feed. 'Metabolisable energy' is simply that component of total energy of an animal feed that is metabolised by an animal. Energy that is not metabolisable is 'excreted energy'. Another way of defining 'metabolisable energy' is to refer to an 'apparent metabolisable energy value' or 'AME value'. An 'AME value' is simply the gross energy of the feed consumed minus the gross energy contained in the faeces, urine, and gaseous products of digestion.

As described herein, the inventors have shown that the energy of an animal feed containing synergistic amounts of BHCl and phytase is greater than the sum of the energy utilisation in a feed containing BHCl only, or phytase only. In this context, the inventors have found a synergistic relationship as between BHCl and phytase in the context of energy utilisation. Accordingly, the AME value of an animal feed containing the BHCl/phytase combination is greater than the AME value of a feed which does not contain this combination.

The finding of the synergistic response is particularly surprising given that, as shown herein, BHCl tends to decrease energy utilisation, and given that phytase has been generally used to increase growth performance via release of phytate-bound phosphate, rather than through improvements in AME.

The invention is particularly important in that it enables one to minimise the input costs associated with animal production. Specifically, as described herein, the invention enables the minimisation of nutritive or non nutritive components without minimising the metabolisable energy of feed, and importantly, without impacting on growth performance. A "nutritive component" or "nutrient component" generally refers to an ingredient of animal feed that imbues the feed with a particular calorific value. "Macronutrients", such as starches, proteins, fats, oils and fibres generally provide the bulk of the energy of an animal feed. "Micronutrients" generally have minimal inherent calorific value, and their core function is to enable the metabolism of the macronutrients. Examples of micronutrients include vitamins, minerals and amino acids.

Thus in one embodiment there is provided an animal feed including:
a nutrient component including one or more of a carbohydrate, fat and protein;
a phytase; and
BHCl.

The feed is characterised in that the BHCl and phytase are provided in the feed in a ratio of amounts of BHCl:phytase so that the AME value of the animal feed equals the AME value of the nutrient component in the presence of the amounts of BHCl and phytase.

According to the invention, it is the synergy arising from the ratio of amounts of BHCl:phytase in the presence of the nutrient component, from which the AME value of the feed arises. More specifically, while the BHCl and phytase do not of themselves have an inherent calorific value relevant to the animal feed, it is the presence of BHCl and phytase in the animal feed which increases the metabolisable energy of the nutrient components of the animal feed. Specifically, in one example disclosed herein, a control diet supported an AME of 12.33 MJ/kg. Individually, BHCl addition increased this by 0.44 MJ to 12.77 MJ/kg, phytase addition marginally decreased this by 0.02 MJ to 12.31 MJ/kg, while in combination, BHCl addition with phytase addition generated an increase of 1.10 MJ/kg (13.43 versus 12.33 MJ/kg), which is indicative of a synergistic response in energy utilisation.

The BHCl and phytase are provided in the animal feed in synergistically effective amounts. 'Synergistically effective amounts' of these components are amounts that provide for an energy utilisation (or AME) that is greater than the sum of the energy utilisation in a feed that includes phytase only, or BHCl only. Therefore, in one embodiment there is provided an animal feed including:
a nutrient component including one or more of a carbohydrate, fat and protein;
a phytase; and
BHCl,
wherein the phytase and BHCl are provided in the feed in synergistically effective amounts.

In one embodiment, the BHCl and phytase are provided in a ratio of about:
0.5 g to 5 g BHCl/kg of feed:100 to 5000 FTU/kg of feed.

'FTU' refers to 'phytase unit'. One FTU is the activity of phytase required to liberate 1 µmol of inorganic phosphorus per minute at pH 5.5 from an excess of 15 M sodium phytate at 37° C.

Preferably the BHCl and phytase are provide in a ratio of about:
1 g to 3 g BHCl/kg of feed:300 to 2000 FTU/kg of feed.

More preferably, the BHCl is provided in an amount of more than 2 g to about 2.75 g/kg of feed, more preferably, about 2.05 g, or 2.1 g, or 2.2 g, or 2.3 g, or 2.4 g or 2.5 g, or 2.6 g, or 2.7 g/kg of feed.

The phytase may be provided in an amount of more than 1000 FTU to about 3000 FTU/kg feed, for example from, about 1,100 FTU or, 1,200 FTU or, 1,300 FTU or, 1,400 FTU or, 1,500 FTU or, 1,600 FTU or, 1,700 FTU or, 1,800 FTU or, 1,900 FTU or, 2,000 FTU or, 2,100 FTU or, 2,200 FTU or, 2,300 FTU or, 2,400 FTU or, 2,500 FTU/kg feed.

In another embodiment, the phytase may be provided in an amount of from 500 FTU, or 600 FTU, or 700 FTU, or 800 FTU, or 900 FTU, or 1,000 FTU/kg of feed. In this embodiment, the BHCL may be provided in an amount of from 2.05 g, or 2.1 g, or 2.2 g, or 2.3 g, or 2.4 g or 2.5 g, or 2.6 g, or 2.7 g/kg of feed.

In a particularly preferred embodiment, the phytase is provided in an amount of about 500 FTU/kg of feed and the BHCl is provided in an amount of about 2 g/kg feed.

An amount of 300 to 2000 FTU/kg of feed would generally equate to about 100 to 500 g phytase/tonne of feed, although of course this is dependent on the concentration enzyme.

As described herein, the invention enables the minimisation of nutritive components of animal feeds without impacting on energy utilisation or growth performance. For example, the invention enables the formation of feeds that have amounts of carbohydrate, fat or protein component that are less than the amount of these components that are conventionally used in specific animal feeds. By way of example, poultry feed normally contains starch in an amount of 300 to 500 g/kg feed, protein in an amount of 150-250 g/kg, fats or oils in an amount of 50 to 80 g/kg and 100-150 g/kg fibre. Other micronutrients include NaCl, lysine, methionine, threonine, NaHCO3, limestone and inorganic phosphate, enzymes, and vitamin and mineral premix. According to the invention, the amount of components of feed may be reduced so that the AME of the nutrient component of the feed (i.e. in the absence of the BHCl/phytase combination) is greater than 9 MJ/kg of feed and no more than about 11 MJ/kg of feed, preferably about 10 MJ/kg of feed to less than about 11 MJ/kg of feed. This represents an AME reduction of about 1 to 2 MJ/kg of the nutrient components, otherwise expressed as about a 4 to 10% reduction.

In one embodiment, the nutrient component of the animal feed of the invention includes:
  starch in an amount of not more than about 270 g/kg feed, for example in a range of from 15 to 270 g/kg feed,
  protein in an amount of 150-250 g/kg feed
  fats or oils in an amount of 50 to 80 g/kg feed and
  fibre in an amount of 100-150 g/kg feed.

In a particularly preferred embodiment there is provided an animal feed including:
  a nutrient component including one or more of a carbohydrate, fat and protein;
  a phytase; and
  BHCl,
  wherein the phytase and BHCl are provided in the feed in synergistically effective amounts, and
  wherein the nutrient component includes starch in an amount of not more than about 270 g/kg feed, for example in a range of from 15 to 270 g/kg feed, In another embodiment, the nutrient component of the animal feed of the invention includes:
  starch in an amount of 300 to 500 g/kg feed
  protein in an amount of 150-250 g/kg feed
  fats or oils in an amount of not more than about 45 g/kg feed and
  fibre in an amount of 100-150 g/kg feed.

In a particularly preferred embodiment there is provided an animal feed including:
  a nutrient component including one or more of a carbohydrate, fat and protein;
  a phytase; and
  BHCl,
  wherein the phytase and BHCl are provided in the feed in synergistically effective amounts, and
  wherein the nutrient component includes fats or oils in an amount of not more than about 45 g/kg feed, preferably about 20 g to 45 g/kg feed.

In one embodiment, the nutrient component of the animal feed of the invention includes:
  starch in an amount of 300 to 500 g/kg feed
  protein in an amount of 150-250 g/kg feed
  fats or oils in an amount of 50 to 80 g/kg feed and
  fibre in an amount of 100-150 g/kg feed,
  the component characterised in that it does not contain one or more of the following micronutrients as an additive or synthetic component: methionine, choline, lysine, threonine, and inorganic phosphate.

In a particularly preferred embodiment there is provided an animal feed including:
  a nutrient component including one or more of a carbohydrate, fat and protein;
  a phytase; and
  BHCl,
  wherein the phytase and BHCl are provided in the feed in synergistically effective amounts, and
  wherein the nutrient component does not include micronutrients as an additive or synthetic component such as methionine, choline, lysine, threonine, and inorganic phosphate.

Further to the above, the invention enables the minimisation of non nutritive components of animal feeds, again without impacting on energy utilisation or growth performance. The decrease in the amount of phytase required according to the invention compared with conventional phytase usage is significant from an economic perspective. For example, a reduction in the amount of phytase equates to a reduction in cost of up to about 3$/tonne of feed.

In those animal feeds where phytase is not used, it is necessary to supplement the feed with phosphate because much of the phytase derived from carbohydrate cannot be released by the animal. The invention is particularly advantageous in this context because it minimised the cost input of both the amount of phytase required an enables one to minimise or avoid providing free phosphate.

The invention is applicable to the production of a variety of animal feeds, and especially to feeds for monogastric animals and livestock, rather than to ruminant animals. Examples include poultry, pork and aquaculture.

Poultry feed is a particularly preferred example of animal feed. As described herein, poultry diets are composed primarily of a mixture of several feedstuffs containing nutritive components, examples of which include cereal grains, soybean meal, animal by-products (such as blood and bone), fats and mineral and vitamin premixes including anhydrous betaine.

In one embodiment, the nutrient component, phytase and BHCl are combined to form a composition suitable for consumption by an animal. Examples of suitable compositions include granules, pellets and the like.

In another embodiment, the nutrient component and phytase are combined to form a composition suitable for consumption by an animal. The composition may not include BHCl. In this embodiment, the BHCl may be provided to the animal as a separate composition i.e. separate to the composition including the nutrient component and phytase. In one example, the BHCl may be provided in drinking water.

In another embodiment there is provided an animal feed premix, said premix consisting of:
a non-nutrient component;
wherein the non-nutrient component includes BHCl and phytase.

Preferably the BHCl and phytase are provided in synergistically effective amounts.

More preferably the non-nutrient component further includes one or more components selected from the group consisting of an enzyme, a pigment, a growth factor, an anti-microbial agent, such as an antibacterial compound for inducing or enhancing growth performance, and an anti-coccidial agent.

In another embodiment there is provided an animal feed premix, said premix consisting of:
a non-nutrient component;
a micronutrient component;
wherein the non-nutrient component includes BHCl and phytase.

More preferably the non-nutrient component further includes one or more components selected from the group consisting of an enzyme, a pigment, a growth factor, an anti-microbial agent, such as an antibacterial compound for inducing or enhancing growth performance.

Preferably the micronutrient component includes a component selected from the group consisting of a vitamin, a mineral and an amino acid.

The animal feed premix according to the invention may be provided in the form of a solid or liquid. Preferably the premix is provided in the form of a solid, such as a granule or a pellet.

In a preferred embodiment of the invention, the phytase is of bacterial origin, preferably having an amino acid sequence of an *E. coli* phytase.

Example

Objective

The present study was designed to evaluate the inclusions of exogenous phytase and betaine hydrochloride, individually and in combination, in broiler diets with three tiers of nutrient specifications.

The composition and nutrient specifications of the three basal starter (1-16 days post-hatch) and finisher (17-37 days post-hatch) diets are shown in Table 1. An NSP-degrading enzyme (Econase XT) was included across all the wheat-based diets to reflect standard practice and the finisher diets contained 20 g/kg Celite as an acid insoluble ash dietary marker. The starter diets were fed as mash, while the finisher diets were steam-pelleted at a conditioning temperature of 85° C. The NC1 diets were the 'phytase-modified' diets with formulated with reductions of 1.4 g/kg Ca and 1.5 g/kg P in the starter diets, which mainly stemmed from the elimination of dicalcium phosphate. The corresponding reductions in the finisher diets were 1.2 g/kg Ca and 1.4/kg P. The NC2 diets were the 'betaine-modified' diets in which energy density, methionine and choline levels were reduced mainly by lower inclusion levels of canola oil and synthetic methionine and the elimination of choline chloride relative to the PC diets. The energy densities were reduced from 12.55 to 12.24 MJ/kg in the starter diets and from 12.97 to 12.66 MJ/kg in the finisher diets. Methionine levels were reduced from 4.44 to 3.19 g/kg in the starter diets and from 4.18 to 2.93 g/kg in the finisher diets. Exogenous phytase (Quantum® Blue; AB Vista) was included in the relevant diets at 100 g per tonne or 500 FTU/kg phytase activity and, similarly, betaine HCl (Hi Beta™, 970 g/kg betaine hydrochloride; Rural Chemical Industries) was included in the diets at 2.75 g/kg.

The betaine-supplemented, experimental diets were analysed for betaine HCl contents by spectrometry (Appendix I). The data indicates that the six betaine-supplemented starter diets contained an average of 3.727 g/kg betaine HCl the six betaine-supplemented finisher diets contained an average of 2.943 g/kg betaine HCl. The 'background' dietary betaine levels were not determined; however, it appears that dietary levels of betaine HCl were higher than intended. All experimental diets were analysed for phytase activity by AB Vista using a modified ELISA method (Appendix II). The data indicates that the six phytase-supplemented starter diets contained an average of 691 FTU/kg phytase activity and the six phytase supplemented finisher diets contained an average of 589 FTU/kg phytase activity. The non-phytase supplemented diets all contained less than 50 FTU/kg phytase activity.

The parameters evaluated included growth performance (weight gains, feed intakes, feed conversion ratios; FCR) from 1 to 16, 17 to 37 and 1 to 37 days post-hatch, 1 to 37 days weight gain-corrected FCR, mortality/cull rates, percentage toe ash, nitrogen (N) excretion and nutrient utilisation. Nutrient utilisation included apparent metabolisable energy (AME), expressed as both MJ/kg and MJ/day, N retention and N-corrected AME (AMEn). Also, breast weights in absolute and relative (% yield) terms, abdominal fat pad weights and pH of gizzard contents were determined. However, for reasons of practical expediency, absolute breast weights were determined on a 'bone-in' basis from birds that had not been de-feathered and this approach inflates both the absolute weight and yield; nevertheless, the data remains indicative. The experimental data was obtained and calculated via standard procedures followed by the Poultry Research Foundation. While the various procedures are not detailed in this report the majority of them have been described in detail (Selle et al., 2003b) previously.

The experimental data was statistically analysed as a 3×2×2 factorial array of dietary treatments. That is diet type (PC, NC1, NC2), without and with the addition of phytase, without and with the addition of betaine HCl. Each of the 12 dietary treatments was offered to 8 replicate cages of 6 birds or a total of 96 cages and 576 birds (male Ross 308 chicks). The IBM® SPSS® Statistics 20 program was used to analyse experimental data and the study complied with specific guidelines of the Animal Ethics Committee of Sydney University.

Results

The effects of dietary treatments on growth performance from 1 to 16 days post-hatch are shown in Table 2 where there were no significant interactions between main effects. The weight gain, feed intake and feed efficiency of birds offered PC diets were superior (P<0.005) to those on NC1 and NC2 diets. For example, the weight gain on PC diets (444 g/bird) was 10.2% higher than NC1 diets (403 g/bird) and 16.8% higher than NC2 diets (380 g/bird). Betaine HCl significantly enhanced feed efficiency by 3.77% (1.380 versus 1.434; P<0.015) in the starter phase and phytase tended to improve weight gain by 4.68% (416 versus 4.01 g/bird; P<0.06) that closely approached significance. Phytase, individually or in tandem with betaine HCl, improved average weight gain, feed intake and feed efficiency by 13.1, 7.44 and 5.26%, respectively, relative to the NC1 control diet and the average FCR (1.387) was very comparable to the PC control diet (1.381).

The effects of dietary treatments on growth performance from 17 to 37 days post-hatch are shown in Table 3 where there were significant two-way interactions between all main effects for weight gain but not for the other parameters. The addition of phytase to the NC1 diet significantly increased weight gain by 10.8% (1827 versus 1649 g/bird) but increases in the PC (4.18%) and NC2 (1.16%) diets were of more modest magnitudes. The addition of betaine HCl to the NC1 diet did not influence weight gain (1737 versus 1739 g/bird) but betaine significantly depressed weight gain when added to the PC and NC2 diets by 6.35 and 6.27%, respectively. Individually, betaine HCl significantly depressed weight gain of the non-supplemented diets by 7.70% (1797 versus 1947 g/bird) but in tandem with phytase there was no difference in weight gain (1953 versus 1947 g/bird) thus the combination of phytase and betaine HCl resulted in a 8.68% weight gain improvement in comparison to betaine HCl on its own (1953 versus 1797 g/bird). Taking the main effects in isolation, the weight gain of the NC2 diet was significantly inferior to the PC and NC2 diets by 14.3 and 12.8%, respectively. Phytase significantly increased weight gain by 5.07% but betaine depressed weight gain by 4.48%. The feed intake of NC1 diets was significantly inferior to both the PC and NC2 diets by 7.60 and 7.91%, respectively, and phytase significantly increased feed intake by 3.95% (3286 versus 3161 g/bird; P<0.02). The feed conversion ratio of NC1 diets was significantly inferior to both the PC and NC2 diets by 7.91 and 5.52%, respectively, and betaine HCl significantly depressed feed efficiency by 2.46% (1.707 versus 1.666; P<0.02).

The effects of dietary treatments on growth performance from 1 to 37 days post are shown in Table 4 and, again, there were significant interactions between main effects for weight gain but not for feed intake and feed conversion ratios. Phytase fractionally increased weight gain by 0.97% in NC2 diets and by 3.71% in PC diets, which was significant. However, phytase addition to NC1 diets resulted in a significant increase with a greater magnitude of 10.6% (2249 versus 2033 g/bird). Betaine HCl significantly depressed weight gains of both the PC and NC2 diets by 4.90 and 5.29%0, respectively. In contrast, however, betaine addition to NC1 diets fractionally improved weight gain by 0.61% (2437 versus 2147 g/bird). Interestingly, the combined inclusion of betaine HCl and phytase, in comparison to betaine HCl alone, resulted in a significant improvement in weight gain of 7.71% (2374 versus 2202 g/bird).

The effects of dietary treatments on gain-corrected feed conversion ratios, mortality/cull rates to 37 days post-hatch, bone mineralisation (% toe ash) and N excretion are shown in Table 5. There were no significant interactions between main effects for gain-corrected FCR; however, each of the main effects did have significant impacts. The gain-corrected FCR for PC diets of 1.521 was significantly better than NC2 diets (1.616) by 5.88% and NC1 diets (1.769) by 16.3%. Also, NC2 diets were significantly better by 8.65% than NC1 diets. Phytase significantly enhanced gain-corrected FCR by 3.72% (1.604 versus 1.666; P<0.03); however, betaine HCl significantly depressed gain-corrected FCR by 3.42% (1.663 versus 1.608; P<0.05). The overall mortality/cull rate was 4.51% but was unrelated to treatments. Phytase increased toe ash by 5.95% (12.47 versus 11.76%; P<0.01), which was the only significant effect observed in respect of bone mineralisation. Betaine HCl reduced N excretion by 7.69% (38.79 versus 42.02 g/bird; P<0.005), which was the only significant effect observed. However, phytase numerically reduced N excretion by 3.93% (39.59 versus 41.21 g/bird; P<0.15). Interestingly, across all three diet types, the lowest N excretion rates were observed in diets supplemented with both betaine HCl and phytase.

The effects of dietary treatments on nutrient utilisation are shown in Table 6. Significant interactions were observed for AME (MJ/kg) between diet type and betaine addition (P<0.05) and between additions of betaine and phytase (P<0.01). The addition of betaine to NC1 diets increased AME by 0.78 MJ (13.10 versus 12.32 MJ/kg); whereas, additions to PC diets resulted in a comparatively modest increase of 0.20 MJ and to NC2 diets a slight decrease of 0.08 MJ. In the absence of phytase, betaine addition resulted in a numerical decrease of 0.08 MJ. However, in the presence of phytase, betaine addition generated an increase of 0.67 MJ (13.68 versus 13.01 MJ/kg). Taken separately, there were significant outcomes for the three main effects of diet type (P<0.001) and also phytase and betaine additions. NC1 diets (12.71 MJ/kg) had significantly lower energy densities than either PC (13.53 MJ/kg) or NC2 (13.30 MJ/kg) diets. Phytase increased AME by 0.34 MJ/kg (13.35 versus 13.01 MJ/kg; P<0.02) and betaine increased AME by 0.30 MJ/kg (13.33 versus 13.03 MJ/kg; P<0.04).

One significant interaction was observed for AME (MJ/day), which was between additions of betaine and phytase (P<0.005). In the absence of phytase, betaine addition depressed energy intake by 0.115 MJ or 5.43% (2.002 versus 2.117 MJ/day). However, in the presence of phytase, betaine addition enhanced energy intake 0.120 MJ or 5.63%/o (2.251 versus 2.131 MJ/day). Taken separately, both diet type and phytase addition significantly influenced energy intake; whereas, betaine did not influence this parameter (P>0.90). The energy intake of NC1 diets (1.940 MJ/day) was inferior to both PC (2.234 MJ/day) and NC2 (2.200 MJ/day) diets. Phytase addition increased energy intake by 0.132 MJ/day or 6.41% (2.191 versus 2.059 MJ/day; P<0.001).

Overall, the birds retained 52.12% N; however, there were no significant treatment effects observed for N retention. There were two significant interactions between main effects for N-corrected AME; these were for diet type×betaine HCl (P<0.01) and phytase×betaine HCl (P<0.03). The addition of betaine HCl to NC1 diets increased AMEn by 1.01 MJ (11.36 versus 10.67 MJ/kg), which was considerably more pronounced than the corresponding increases in PC (0.23 MJ) and NC2 (0.17 MJ) diets. In the absence of phytase, betaine HCl increased AMEn by 0.20 MJ (11.46 versus 11.26 MJ/kg). However, in the presence of phytase, betaine HCl increased AMEn by 0.74 MJ (12.13 versus 11.39 MJ/kg), which is also a considerably more pronounced response. Taken in isolation, all three main effects had significant impacts on AMEn. The NC1 diets were significantly inferior to both PC and NC2 diets. Phytase increased AMEn by 0.40 MJ or 3.52% (11.76 versus 11.36 MJ/kg; P<0.005) and betaine HCl increased AMEn by 0.46 MJ or 4.06% (11.79 versus 11.33 MJ/kg; P<0.001)

The effects of dietary treatments on absolute and relative breast weights, fat pad weights and gizzard pH are shown in Table 7. There was a significant interaction (P<0.005) between diet type and phytase addition for absolute breast weights. Phytase increased breast weights by 12.9% in NC1 diets (603 versus 534 g/bird) but the improvement was a more modest increase of 5.87% in PC diets (703 versus 664 g/bird) with no real difference in NC2 diets (628 versus 634 g/bird). As main effects, there were significant differences between PC (683 g/bird), NC2 (630 g/bird) and NC1 (568 g/bird) diets. Also phytase significantly increased absolute breast weights by 5.57% (644 versus 610 g/bird; P<0.001) but betaine addition had no influence (P>0.40). There was a significant interaction (P<0.015) between phytase and betaine additions for relative breast weights or percentage yield. In the absence of phytase, betaine HCl increased yield from 25.9 to 27.0%, but, in the presence of phytase, betaine HCl fractionally decreased breast yield from 26.5 to 26.4%. The main effect of diet type was significant (P<0.001) where the yield on PC diets (27.49%) was superior to NC1 (25.9%) and NC2 (26.1%) diets. Betaine HCl increased breast yield by 0.5 percentage units (26.7 versus 26.2%; P<0.05) but phytase had no influence (P>0.90) on this parameter.

There was a significant interaction (P<0.005) between phytase and betaine additions for fat pad weights. In the absence of phytase, betaine HCl decreased fat pad weights by 17.6% (16.8 versus 20.4 g/bird), but, in the presence of phytase, betaine HCl increased fat pad weights by 8.67% (21.3 versus 19.6 g/bird). The main effect of diet type was significant (P<0.001) where fat pad weights on NC1 (16.6 g/bird) diets were less than both PC (20.3 g/bird) and NC2 (21.7 g/bird) diets. Phytase increased fat pad weights by 10.2% (20.5 versus 18.6 g/bird; P<0.04) but betaine HCl had no effect (P>0.25) on this parameter.

The pH of digesta in the gizzard was determined for birds offered PC and NC diets and was analysed as a 2×2×2 factorial array of treatments where there were no significant interactions between main effects. Gizzard pH of NC1 diets was significantly lower than PC diets (3.46 versus 3.61; P<0.05); however, phytase had no effect (P>0.50) on gizzard pH. In contrast, betaine HCl significantly reduced gizzard pH by 0.28 (3.39 versus 3.67; P<0.005).

Discussion

The 2012 Aviagen performance objectives for male Ross 308 chicks at 37 days post-hatch is for a body weight of 2457 g, a feed intake of 3944 g and an FCR of 1.605. If the 42 g day-old chick weight is deducted this translates to a weight gain of 2415 g and an FCR of 1.633. In the present study, birds offered the non-supplemented PC diets had a weight gain of 2530 g and an FCR of 1.591, which represents respective improvements of 4.76% and 2.57% relative to the performance objectives.

As tabulated, meat-and-bone meal was analysed to contain 4.17 g/kg P and it is assumed that dicalcium phosphate contained 180 g/kg P. Samples of wheat and soybean meal were analysed by an external laboratory and were reported to contain 2.50 and 6.65 g/kg total P, respectively. Unfortunately, however, the phytate-P levels reported were not credible and these values were estimated from locally generated data (Selle et al., 2003b) on the basis of total P contents because the two parameters are significantly correlated. On this basis, wheat and soybean meal contained estimated levels of 1.85 and 4.53 g/kg phytate-P, respectively. Thus the estimated total P, phytate-P and non-phytate-P concentrations of the six basal diets are shown in Table 1; on average, the diets contained 4.34 g/kg total P, 2.45 g/kg phytate-P and 1.85 g/kg nonphytate-P. Thus, there was a moderate substrate level of 8.69 g/kg phytate or 2.45 g/kg phytate-P. However, the estimated average levels of 4.34 g/kg total P and 1.85 g/kg nonphytate-P, especially the latter, do appear suspiciously low given the growth performance of the birds offered these diets. The reported 2.50 g/kg total P concentration in wheat does appear low as Selle et al. (2003b) reported an average total P content of 3.08 g/kg in 37 wheat samples.

The estimated nonphytate-P levels in the NC1 starter and finisher diets of 1.157 and 1.825 g/kg, respectively, are noticeably less that the specified available P levels of 2.50 and 2.00 g/kg respectively. Therefore, it is noteworthy that toe ash was numerically lowest in NC1 diets and, overall, phytase significantly increased toe ash by 6.04% (12.47 versus 11.76 g/kg; P<0.01). Moreover, specifically in the NC1 diets, phytase supplementation increased average toe ash by 8.66% (12.42 versus 11.43%). The likelihood is that the diets were limiting in either nonphytate or available P, which would amplify responses to phytase; whereas, as would be expected, betaine HCl did not have a significant influence on toe ash (12.07 versus 12.15%; P>0.75).

In the discussion that follows the initial focus is on the impact of diet type, mainly on growth performance. Secondly, the main effects of betaine HCl and phytase on the parameters assessed will be considered, followed by assessments of the interactions between the dietary inclusions of phytase and betaine HCl.

From 1 to 37 days post-hatch, weight gains of birds offered the non-supplemented NC1 diet was 18.9% less than the control PC diet (2053 versus 2530 g/bird) but phytase plus betaine HCl supplementation of NC1 diets generated a 11.2% increase in weight gain (2282 versus 2053 g/bird) so that the deficit to the PC diet was 9.8%. Feed intakes followed a similar pattern with a 13.2% reduction with the transition from PC to NC1 control diets (3495 versus 4025 g/bird) and phytase supplementation of the NC1 diet generated a 7.9% increase in feed intake (3770 versus 3495 g/bird). The FCR of control PC diets was 1.591 and the FCR of control NC1 diets was 1.704, which represents a 7.10% deterioration in feed efficiency; however phytase plus betaine HCl supplementation of the NC1 diet increased feed efficiency by 3.81% (1.639 versus 1.704). Thus phytase supplementation of NC1 diets partially compensated the reductions in growth performance parameters generated by the transition from PC to NC1 control diets. That this compensation was partial may be attributed to very low non-phytate P levels in the NC1 diets coupled with relatively modest levels of the substrate, phytate.

The reductions in performance parameters arising from the transition from PC to NC2 control diets were considerably more modest with reductions of 3.2%, 2.8% and 0.4% in weight gain, feed intake and FCR, respectively. The inclusion of betaine HCl and phytase in NC 2 diets generated a small 1.1% increase in feed intake (3955 versus 3911 g/bird) but betaine HCl and phytase, singly and in combination, did not enhance either weight gain or feed conversion ratios supported by NC2 diets.

The influences of diet type and supplementation on N-corrected AME are of interest. The transition from control PC to NC1 diets reduced AMEn by 9.4% or 1.11 MJ/kg (10.70 versus 11.81 MJ/kg). However, phytase plus betaine HCl supplementation of NC 1 diets increased AMEn by 13.1% or 1.40 MJ or (12.10 versus 10.70 MJ/kg) resulting in a higher AMEn value by 0.29 MJ (2.46%) than the control PC diet, which is a noteworthy outcome. The transition from PC to NC2 control diets reduced AMEn by 4.49% or 0.53 MJ (11.28 versus 11.81 MJ/kg); however, phytase plus betaine HCl supplementation of NC2 diets increased AME by 6.29% or 0.71 MJ/kg (11.99 versus 11.28 MJ/kg), which was 0.18 MJ (1.52/o) higher than the control PC diet. Thus phytase and betaine HCl in tandem highly were effective in enhancing nutrient utilisation as assessed by N-corrected AME.

As growth performance main effects, phytase significantly (P<0.001) increased weight gain by 5.07% in the finisher phase and by 4.84% from 1 to 37 days post-hatch. In addition, phytase significantly (P<0.01) increased feed intake by 3.76% over the entire feeding period and also significantly (P<0.03) improved weight gain-corrected FCR by 3.72%. This finding is noteworthy as positive growth performance responses to phytase are often confined to weigh gain and feed intake rather than efficiency of feed conversion. Phytase supplementation of NC 1 diets generated robust improvements of 10.6% in weight gain, 7.63% in feed intake and 2.79% in feed conversion from 1 to 37 days post-hatch.

As nutrient utilisation main effects, phytase significantly increased AME by 0.34 MJ/kg (P<0.02) and 0.132 MJ/day (P<0.001) and AMEn by 0.40 MJ/kg (P<0.005), which are tangible responses in energy utilisation. Somewhat curiously, the 3×2×2 factorial array of treatments, including phytase, did not significantly influence N retention. Phytase significantly increased (P<0.04) abdominal fat pad weights by 10.2%, which may be an indicator of enhanced energy utilisation.

The significant main effects of betaine HCl on growth performance included an improvement of 3.77% in FCR in the starter phase but, alternatively, a depression of 2.46% in the finisher phase such that there was no significant impact (P>0.30) from 1 to 37 days post-hatch. However, betaine HCl significantly depressed growth rates in the finisher phase by 4.48% and by 3.38% over the entire feeding period, which suggests the 2.75 g/kg inclusion rate may have been excessive.

Of interest is that betaine HCl significantly (P<0.005) reduced N excretion by 7.69% from 42.02 to 38.79 g/bird during the total excreta collection period. This is an important outcome given the obvious environmental implications. Also, as a main effect, betaine HCl significantly enhanced energy utilisation by either 0.30 MJ/kg as AME or 0.46 MJ/kg as AMEn. Importantly, betaine HCl significantly (P<0.05) increased breast meat yield by 1.91% from 26.2 to 26.7% as a main effect. Finally, betaine HCl significantly reduced (P<0.005) the pH of gizzard contents from pH 3.67 to 3.39, which may advantage the activity of the *E. coli*-derived phytase given its pH activity spectrum.

The significant interactions observed between the dietary additions of betaine HCl and phytase are of particular relevance. There was a significant interaction (P=0.003) between betaine HCl and phytase for weight gain from 17 to 37 days post-hatch. Betaine HCl alone (2.943 g/kg analysed) depressed weight gain by 7.70% (1797 versus 1947 g/bird) but in the presence of phytase (589 FTU/kg analysed) there was a fractional increase in weight gain of 0.31% (1953 versus 1947 g/kg). Thus the use of phytase and betaine HCl in tandem increased weight gain by 8.68% (1953 versus 1797 g/bird) relative to the use of betaine HCl alone. In addition, there was a significant interaction (P=0.009) between betaine HCl and phytase for weight gain, with a similar outcome, from 1 to 37 days post-hatch. The inclusion of betaine HCl at 2.75 g/kg notionally may have been excessive and, if so, the analysed concentrations (3.727 and 2.943 g/kg) would have exacerbated the situation. Nevertheless, it appears that phytase attenuated the negative impact of possibly excessive betaine HCl inclusion levels.

Significant interactions involving nutrient utilisation were also observed between betaine HCl and phytase for AME expressed as MJ/kg (P=0.009) and MJ/day (P=0.001) and N-corrected AME (P=0.022). For example, betaine HC alone slightly depressed AME (MJ/kg) by 0.08 MJ but in tandem with phytase there was a substantial increase in AME of 0.67 MJ/kg. Thus the betaine HCl and phytase interaction for AME followed the same pattern that was in evidence for weight gain.

In respect of carcass traits there were significant interactions between betaine HCl and phytase for breast meat yield (P=0.011) and abdominal fat pad weights (P=0.002). Here betaine HCl alone increased breast meat yield from 25.9 to 27.0% but in combination with phytase there was a fractional depression in yield from 26.5 to 26.4%. Also betaine HCl alone decreased fat pad weight from 20.4 to 16.8 g/bird but in combination with phytase there was an increase from 19.6 to 21.3 g/bird. Thus the interactive patterns for these two carcass traits were quite different for those observed between betaine HCl and phytase for weight gain and energy utilisation.

It is instructive to compare the tandem inclusion of phytase and betaine HCl with their individual inclusions. For example, for 1 to 37 days post-hatch weight gain the tandem inclusion generated a weight gain of 2282 g/bird in NC1 diets. This was 3.02% higher than phytase alone (2215 g/bird) and 3.42% higher than betaine HCl alone (2012 g/bird). Similarly, phytase plus betaine HCl supported a feed conversion ratio of 1.639 in NC1 diets over both feeding phases. This represented improvements in feed efficiency of 3.64% relative to phytase alone (1.701) and an improvement of 5.37% relative to betaine HCl alone (1.732).

Of real interest is the effect of dietary inclusions in NC2 diets on N excretion. Birds offered NC2 control diets excreted 45.68 g/bird N. Betaine HCl reduced this figure by 7.03% to 42.47 g/bird and phytase reduced this figure by 10.7% to 40.80 g/bird. However, the combination of phytase and betaine HCl generated a fully additive reduction in N excretion of 18.9% (37.05 versus 45.68 g/bird).

Finally, the effect of dietary inclusions on AME (MJ/kg) in NC1 diets is considered. The control diet supported an energy density of 12.33 MJ/kg. Individually betaine HCl increased this by 0.44 MJ to 12.77 MJ/kg and, somewhat surprisingly, phytase marginally decreased this by 0.02 MJ to 12.31 MJ/kg. However, in combination, betaine HCl plus phytase generated an increase of 1.10 MJ/kg (13.43 versus 12.33 MJ/kg), which does appear to be a synergistic response.

REFERENCES

Selle P H et al. 2003(b) *Aust. J. Exper. Agricul.* 45:475-479

TABLE 1

Composition and nutrient specifications of basal diets [phytase (0.100 g/kg) and betaine HCl (2.750 g/kg) were added to the appropriate diets at the expense of wheat]

| Item (g/kg) | Starter diets | | | Finisher diets | | |
| --- | --- | --- | --- | --- | --- | --- |
| | PC | NC1 | NC2 | PC | NC1 | NC2 |
| Wheat[1] | 617.9 | 628.3 | 639.10 | 648.5 | 645.8 | 667.0 |
| Soybean meal (48)[2] | 304.0 | 310.0 | 299.0 | 253.4 | 274.0 | 249.6 |

TABLE 1-continued

Composition and nutrient specifications of basal diets [phytase (0.100 g/kg) and betaine HCl (2.750 g/kg) were added to the appropriate diets at the expense of wheat]

| Item | Starter diets | | | Finisher diets | | |
|---|---|---|---|---|---|---|
| (g/kg) | PC | NC1 | NC2 | PC | NC1 | NC2 |
| Meat and bone meal (50)[3] | 30.0 | 22.0 | 30.0 | 30.0 | 10.0 | 30.0 |
| Canola oil | 20.0 | 17.0 | 6.0 | 26.0 | 27.0 | 13.0 |
| Limestone | 6.0 | 9.0 | 6.0 | 6.0 | 11.0 | 6.0 |
| Dicalcium phosphate | 8.0 | 0.0 | 8.0 | 4.0 | 0.00 | 4.0 |
| Sodium chloride | 3.6 | 3.2 | 3.6 | 2.0 | 2.3 | 2.0 |
| Sodium bicarbonate | 2.0 | 2.0 | 2.0 | 2.0 | 2.0 | 2.0 |
| Lysine HCl | 2.4 | 2.4 | 2.5 | 2.4 | 2.3 | 2.4 |
| Methionine | 2.2 | 2.2 | 0.9 | 2.2 | 2.1 | 0.9 |
| Threonine | 0.3 | 0.3 | 0.3 | 0.5 | 0.5 | 0.5 |
| Choline-chloride (60) | 1.0 | 1.0 | 0.0 | 0.4 | 0.4 | 0.0 |
| Vitamin-mineral premix | 2.5 | 2.5 | 2.5 | 2.5 | 2.5 | 2.5 |
| Econase XT | 0.1 | 0.1 | 0.1 | 0.1 | 0.1 | 0.1 |
| Celite | — | — | — | 20.0 | 20.0 | 20.0 |
| Metabolisable energy (MJ/kg) | 12.55 | 12.55 | 12.24 | 12.97 | 12.97 | 12.66 |
| Calcium | 8.40 | 7.00 | 8.40 | 7.40 | 6.20 | 7.40 |
| Available phosphorus | 4.00 | 2.50 | 4.00 | 3.40 | 2.00 | 3.40 |
| Sodium | 2.40 | 2.20 | 2.40 | 1.80 | 1.80 | 1.80 |
| Choline | 1.85 | 1.85 | — | 1.50 | 1.50 | — |
| SID | | | | | | |
| Lysine | 12.0 | 1.2.0 | 12.0 | 11.0 | 11.0 | 11.0 |
| Methionine | 4.44 | 4.44 | 3.19 | 4.18 | 4.18 | 2.93 |
| Methionine and cystine | 8.40 | 8.40 | 7.15 | 8.03 | 8.03 | 6.78 |
| Tryptophan | 1.92 | 1.9.2 | 1.92 | 1.87 | 1.87 | 1.87 |
| Threonine | 7.44 | 7.44 | 7.44 | 7.04 | 7.04 | 7.04 |
| Arginine | 12.60 | 12.60 | 12.60 | 11.88 | 11.88 | 11.88 |
| Isoleucine | 7.80 | 7.80 | 7.80 | 7.37 | 7.37 | 7.37 |
| Valine | 9.24 | 9.24 | 9.24 | 8.58 | 8.58 | 8.58 |
| Estimates | | | | | | |
| Total P | 5.131 | 3.724 | 5.151 | 4.225 | 3.553 | 4.245 |
| Phytate-P | 2.520 | 2.567 | 2.537 | 2.400 | 2.489 | 2.416 |
| Nonphytate P | 2.611 | 1.157 | 2.614 | 1.825 | 1.064 | 1.829 |

[1]Contained 2.50 g/kg P (Symbio Alliance, Job No 196546) and estimated 1.85 g/kg phytate-P,
[2]Contained 6.65 g/kg P (Symbio Alliance, Job No 196546) and estimated 4.53 g/kg phytate-P.
[3]Contained 8.15 g/kg Ca and 4.17 g/kg P (Grain Growers, Job No 02191)

TABLE 2

Effect of dietary treatments on growth performance from 1 to 16 days post-hatch

| Treatments | | | Growth performance | | |
|---|---|---|---|---|---|
| Diet type | Phytase (FTU/kg) | Betaine (g/kg) | Weight gain (g/bird) | Feed intake (g/bird) | Feed efficiency |
| PC | 0 | 0 | 437 | 603 | 1.381 |
|  | 0 | 2.75 | 444 | 591 | 1.334 |
|  | 500 | 0 | 441 | 590 | 1.341 |
|  | 500 | 2.75 | 453 | 596 | 1.318 |
| NC1 | 0 | 0 | 373 | 544 | 1.464 |
|  | 0 | 2.75 | 395 | 556 | 1.414 |
|  | 500 | 0 | 418 | 591 | 1.415 |
|  | 500 | 2.75 | 426 | 578 | 1.359 |
| NC2 | 0 | 0 | 383 | 570 | 1.503 |
|  | 0 | 2.75 | 377 | 523 | 1.394 |
|  | 500 | 0 | 378 | 564 | 1.502 |
|  | 500 | 2.75 | 383 | 557 | 1.462 |
| SEM |  |  | 13.448 | 16.103 | 0.0363 |
| Main effects: Diet type | | | | | |
| PC |  |  | 444[c] | 595[b] | 1.343[c] |
| NC1 |  |  | 403[b] | 567[a] | 1.413[b] |
| NC2 |  |  | 380[a] | 553[a] | 1.465[a] |
| Phytase | | | | | |
| 0 |  |  | 401 | 564 | 1.415 |
| 500 FTU/kg |  |  | 416 | 579 | 1.399 |
| Betaine | | | | | |
| 0 |  |  | 405 | 577 | 1.434[a] |
| 2.75 g/kg |  |  | 413 | 567 | 1.380[b] |
| Significance (P=) | | | | | |
| Diet type (D) |  |  | <0.001 | 0.002 | <0.001 |
| Phytase (P) |  |  | 0.054 | 0.115 | 0.460 |
| Betaine (B) |  |  | 0.313 | 0.279 | 0.012 |
| D × P |  |  | 0.122 | 0.252 | 0.232 |
| D × B |  |  | 0.727 | 0.438 | 0.745 |
| P × B |  |  | 0.935 | 0.552 | 0.492 |
| D × P × B |  |  | 0.798 | 0.371 | 0.759 |

TABLE 3

Effect of dietary treatments on growth performance from 17 to 37 days post-hatch

| Diet type | Phytase (FTU/kg) | Betaine (g/kg) | Weight gain (g/bird) | Feed intake (g/bird) | Feed efficiency |
|---|---|---|---|---|---|
| PC | 0 | 0 | 2094 | 3422 | 1.636 |
|  | 0 | 2.75 | 1878 | 3123 | 1.665 |
|  | 500 | 0 | 2094 | 3340 | 1.597 |
|  | 500 | 2.75 | 2044 | 3328 | 1.627 |
| NC1 | 0 | 0 | 1680 | 2950 | 1.757 |
|  | 0 | 2.75 | 1618 | 2923 | 1.811 |
|  | 500 | 0 | 1798 | 3179 | 1.769 |
|  | 500 | 2.75 | 1857 | 3157 | 1.704 |
| NC2 | 0 | 0 | 2067 | 3342 | 1.617 |
|  | 0 | 2.75 | 1896 | 3205 | 1.691 |
|  | 500 | 0 | 2047 | 3311 | 1.619 |
|  | 500 | 2.75 | 1960 | 3398 | 1.746 |
| SEM |  |  | 34.944 | 81.503 | 0.0532 |
| Main effects: Diet type |  |  |  |  |  |
| PC |  |  | $2027^b$ | $3303^b$ | $1.631^b$ |
| NC1 |  |  | $1738^a$ | $3052^a$ | $1.760^a$ |
| NC2 |  |  | $1993^b$ | $3314^b$ | $1.668^b$ |
| Phytase |  |  |  |  |  |
| 0 |  |  | $1872^a$ | $3161^a$ | 1.696 |
| 500 FTU/kg |  |  | $1967^b$ | $3286^b$ | 1.677 |
| Betaine |  |  |  |  |  |
| 0 |  |  | $1963^b$ | 3257 | $1.666^a$ |
| 2.75 g/kg |  |  | $1875^a$ | 3189 | $1.707^b$ |
| Significance (P=) |  |  |  |  |  |
| Diet type (D) |  |  | <0.001 | <0.001 | <0.001 |
| Phytase (P) |  |  | <0.001 | 0.010 | 0.471 |
| Betaine (B) |  |  | <0.001 | 0.149 | 0.019 |
| D × P |  |  | 0.008 | 0.278 | 0.451 |
| D × B |  |  | 0.013 | 0.428 | 0.252 |
| P × B |  |  | 0.003 | 0.070 | 0.686 |
| D × P × B |  |  | 0.712 | 0.443 | 0.396 |

TABLE 4

Effect of dietary treatments on growth performance from 1 to 37 days post-hatch

| Diet type | Phytase (FTU/kg) | Betaine (g/kg) | Weight gain (g/bird) | Feed intake (g/bird) | Feed efficiency |
|---|---|---|---|---|---|
| PC | 0 | 0 | 2530 | 4025 | 1.591 |
|  | 0 | 2.75 | 2321 | 3714 | 1.601 |
|  | 500 | 0 | 2536 | 3930 | 1.550 |
|  | 500 | 2.75 | 2497 | 3924 | 1.570 |
| NC1 | 0 | 0 | 2053 | 3495 | 1.704 |
|  | 0 | 2.75 | 2012 | 3478 | 1.732 |
|  | 500 | 0 | 2215 | 3770 | 1.701 |
|  | 500 | 2.75 | 2282 | 3735 | 1.639 |
| NC2 | 0 | 0 | 2450 | 3911 | 1.597 |
|  | 0 | 2.75 | 2272 | 3728 | 1.641 |
|  | 500 | 0 | 2425 | 3875 | 1.599 |
|  | 500 | 2.75 | 2344 | 3955 | 1.699 |
| SEM |  |  | 40.529 | 87.166 | 0.0387 |
| Main effects: Diet type |  |  |  |  |  |
| PC |  |  | 2471 | $3898^b$ | $1.578^c$ |
| NC1 |  |  | 2141 | $3619^a$ | $1.694^a$ |
| NC2 |  |  | 2373 | $3867^b$ | $1.634^b$ |
| Phytase |  |  |  |  |  |
| 0 |  |  | 2273 | $3725^a$ | 1.644 |
| 500 FTU/kg |  |  | 2383 | $3865^b$ | 1.626 |
| Betaine |  |  |  |  |  |
| 0 |  |  | 2368 | 3834 | 1.624 |
| 2.75 g/kg |  |  | 2288 | 3756 | 1.647 |
| Significance (P=) |  |  |  |  |  |
| Diet type (D) |  |  | <0.001 | <0.001 | <0.001 |
| Phytase (P) |  |  | <0.001 | 0.007 | 0.429 |
| Betaine (B) |  |  | 0.001 | 0.122 | 0.307 |
| D × P |  |  | 0.004 | 0.204 | 0.324 |
| D × B |  |  | 0.023 | 0.523 | 0.270 |
| P × B |  |  | 0.009 | 0.072 | 0.853 |
| D × P × B |  |  | 0.789 | 0.365 | 0.401 |

TABLE 5

Effect of dietary treatments on gain-corrected feed conversion ratios, mortality/cull rates, bone mineralisation (percentage toe ash) and N excretion during total excreta collection period

| Diet type | Phytase (FTU/kg) | Betaine (g/kg) | Gain-corrected FCR (g/g) | Mortality and cull rates (%) | Toe ash (%) | N excretion (g/bird) |
|---|---|---|---|---|---|---|
| PC | 0 | 0 | 1.510 | 4.18 | 11.30 | 39.97 |
|  | 0 | 2.75 | 1.604 | 4.18 | 11.99 | 40.34 |
|  | 500 | 0 | 1.467 | 8.35 | 12.29 | 39.59 |
|  | 500 | 2.75 | 1.503 | 2.09 | 12.54 | 39.20 |
| NC1 | 0 | 0 | 1.814 | 6.25 | 11.70 | 41.52 |
|  | 0 | 2.75 | 1.858 | 4.18 | 11.15 | 37.30 |
|  | 500 | 0 | 1.747 | 4.18 | 12.62 | 44.54 |
|  | 500 | 2.75 | 1.657 | 6.26 | 12.22 | 36.38 |
| NC2 | 0 | 0 | 1.548 | 2.09 | 12.10 | 45.68 |
|  | 0 | 2.75 | 1.663 | 6.25 | 12.29 | 42.47 |
|  | 500 | 0 | 1.560 | 4.18 | 12.88 | 40.80 |
|  | 500 | 2.75 | 1.692 | 2.09 | 12.24 | 37.05 |
| SEM |  |  | 0.0474 | 3.266 | 0.4171 | 1.8227 |
| Main effects: Diet type |  |  |  |  |  |  |
| PC |  |  | $1.521^a$ | 4.69 | 12.03 | 39.78 |
| NC1 |  |  | $1.769^c$ | 5.21 | 11.92 | 39.93 |
| NC2 |  |  | $1.616^b$ | 3.65 | 12.38 | 41.50 |
| Phytase |  |  |  |  |  |  |
| 0 |  |  | $1.666^a$ | 4.51 | $11.76^a$ | 41.21 |
| 500 FTU/kg |  |  | $1.604^b$ | 4.51 | $12.47^b$ | 39.59 |
| Betaine |  |  |  |  |  |  |
| 0 |  |  | $1.608^b$ | 4.86 | 12.15 | $42.02^b$ |
| 2.75 g/kg |  |  | $1.663^a$ | 4.17 | 12.07 | $38.79^a$ |
| Significance (P=) |  |  |  |  |  |  |
| Diet type (D) |  |  | <0.001 | 0.789 | 0.289 | 0.341 |
| Phytase (P) |  |  | 0.026 | 0.998 | 0.006 | 0.128 |
| Betaine (B) |  |  | 0.046 | 0.713 | 0.755 | 0.003 |
| D × P |  |  | 0.073 | 0.903 | 0.567 | 0.052 |
| D × B |  |  | 0.096 | 0.644 | 0.264 | 0.061 |
| P × B |  |  | 0.291 | 0.463 | 0.448 | 0.409 |
| D × P × B |  |  | 0.532 | 0.431 | 0.711 | 0.761 |

TABLE 6

Effect of dietary treatments on apparent metabolisable energy (AME: MJ/kg, MJ/day), nitrogen (N) retention and N-corrected AME (AMEn)

| Treatments | | AME | | | AMEn |
|---|---|---|---|---|---|
| Diet type | Phytase (FTU/kg) | Betaine (g/kg) | (MJ/kg DM) | AME (MJ/day) | N retention (%) | (MJ/kg DM) |
| PC | 0 | 0 | 13.63 | 2.330 | 55.22 | 11.81 |
|  | 0 | 2.75 | 13.29 | 2.077 | 52.05 | 11.69 |
|  | 500 | 0 | 13.23 | 2.207 | 50.08 | 11.73 |
|  | 500 | 2.75 | 13.96 | 2.324 | 53.72 | 12.30 |
| NC1 | 0 | 0 | 12.33 | 1.818 | 50.80 | 10.70 |
|  | 0 | 2.75 | 12.77 | 1.868 | 52.14 | 11.25 |
|  | 500 | 0 | 12.31 | 1.953 | 50.56 | 10.64 |
|  | 500 | 2.75 | 13.43 | 2.123 | 49.81 | 12.10 |
| NC2 | 0 | 0 | 13.19 | 2.203 | 53.27 | 11.28 |
|  | 0 | 2.75 | 12.86 | 2.061 | 49.25 | 11.43 |
|  | 500 | 0 | 13.50 | 2.233 | 53.30 | 11.80 |
|  | 500 | 2.75 | 13.66 | 2.305 | 55.16 | 11.99 |
| SEM | | | 0.2406 | 0.0570 | 1.9438 | 0.2025 |
| Main effects: Diet type | | | | | | |
| PC | | | $13.53^b$ | $2.234^b$ | 52.77 | $11.88^b$ |
| NC1 | | | $12.71^a$ | $1.940^a$ | 50.83 | $11.17^a$ |
| NC2 | | | $13.30^b$ | $2.200^b$ | 52.74 | $11.62^b$ |
| Phytase | | | | | | |
| 0 | | | $13.01^a$ | $2.059^a$ | 52.12 | $11.36^a$ |
| 500 FTU/kg | | | $13.35^b$ | $2.191^b$ | 52.11 | $11.76^b$ |
| Betaine | | | | | | |
| 0 | | | $13.03^a$ | 2.124 | 52.21 | $11.33^a$ |
| 2.75 g/kg | | | $13.33^b$ | 2.126 | 52.02 | $11.79^b$ |
| Significance (P=) | | | | | | |
| Diet type (D) | | | <0.001 | <0.001 | 0.271 | <0.001 |
| Phytase (P) | | | 0.018 | <0.001 | 0.990 | 0.001 |
| Betaine (B) | | | 0.035 | 0.940 | 0.868 | <0.001 |
| D × P | | | 0.466 | 0.265 | 0.171 | 0.641 |
| D × B | | | 0.040 | 0.071 | 0.851 | 0.007 |
| P × B | | | 0.009 | 0.001 | 0.118 | 0.022 |
| D × P × B | | | 0.683 | 0.303 | 0.208 | 0.301 |

TABLE 7

Effect of dietary treatments on absolute breast weight, breast meat yield, fat pad weights and gizzard pH

| Treatments | | | Breast weight (g/bird) | Breast meat yield (%) | Fat pad weight (g/bird) | Gizzard pH |
|---|---|---|---|---|---|---|
| Diet type | Phytase (FTU/kg) | Betaine (g/kg) | | | | |
| PC | 0 | 0 | 668 | 26.1 | 21.8 | 3.90 |
|  | 0 | 2.75 | 660 | 28.3 | 17.3 | 3.40 |
|  | 500 | 0 | 708 | 27.6 | 21.0 | 3.70 |
|  | 500 | 2.75 | 697 | 27.5 | 21.0 | 3.45 |
| NC1 | 0 | 0 | 541 | 25.7 | 16.4 | 3.58 |
|  | 0 | 2.75 | 526 | 25.7 | 14.7 | 3.35 |
|  | 500 | 0 | 581 | 26.0 | 17.1 | 3.51 |
|  | 500 | 2.75 | 624 | 26.2 | 18.3 | 3.38 |
| NC2 | 0 | 0 | 642 | 25.9 | 23.1 | — |
|  | 0 | 2.75 | 625 | 26.9 | 18.4 | — |
|  | 500 | 0 | 643 | 26.0 | 20.8 | — |
|  | 500 | 2.75 | 612 | 25.5 | 24.7 | — |
| SEM | | | 15.247 | 0.3841 | 1.442 | 0.1057 |
| Main effects: Diet type | | | | | | |
| PC | | | $683^c$ | $27.4^b$ | $20.3^b$ | $3.61^b$ |
| NC1 | | | $568^a$ | $25.9^a$ | $16.6^a$ | $3.46^a$ |
| NC2 | | | $630^b$ | $26.1^a$ | $21.7^b$ | — |
| Phytase | | | | | | |
| 0 | | | $610^a$ | 26.4 | $18.6^a$ | 3.56 |
| 500 FTU/kg | | | $644^b$ | 26.4 | $20.5^b$ | 3.51 |
| Betaine | | | | | | |
| 0 | | | 631 | $26.2^a$ | 20.0 | $3.67^b$ |
| 2.75 g/kg | | | 624 | $26.7^b$ | 19.1 | $3.39^a$ |
| Significance (P=) | | | | | | |
| Diet type (D) | | | <0.001 | <0.001 | <0.001 | 0.044 |
| Phytase (P) | | | <0.001 | 0.930 | 0.030 | 0.540 |
| Betaine (B) | | | 0.436 | 0.041 | 0.257 | 0.001 |
| D × P | | | 0.004 | 0.084 | 0.934 | 0.752 |
| D × B | | | 0.226 | 0.184 | 0.554 | 0.213 |
| P × B | | | 0.434 | 0.011 | 0.002 | 0.251 |
| D × P × B | | | 0.210 | 0.070 | 0.359 | 0.584 |

APPENDIX I

Samples tested as received. On analysis, the following test results were obtained:

| Sample Marking | Feed Form | Inclusion Level | Betaine•HCl (Spectrometry) ppm |
|---|---|---|---|
| 2B-Starter | Mash | 2.75 g/kg | 3693.88 |
| 4D-Starter | Mash | 2.75 g/kg | 3468.93 |
| 6F-Starter | Mash | 2.75 g/kg | 4848.68 |
| 8H-Starter | Mash | 2.75 g/kg | 4312.74 |
| 10J-Starter | Mash | 2.75 g/kg | 2700.45 |
| 12L-Starter | Mash | 2.75 g/kg | 3335.16 |
| 2B-Finisher | Pellet | 2.75 g/kg | 2926.57 |
| 4D-Finisher | Pellet | 2.75 g/kg | 2893.08 |
| 6F-Finisher | Pellet | 2.75 g/kg | 2870.22 |
| 8H-Finisher | Pellet | 2.75 g/kg | 3109.68 |
| 10J-Finisher | Pellet | 2.75 g/kg | 3009.63 |
| 12J-Finisher | Pellet | 2.75 g/kg | 2851.73 |

APPENDIX II

| Sample information | Phytase activity (QB Elisa FTU/kg) | CV (%) |
|---|---|---|
| 1A Starter 0 FTU | <50 | |
| 2B Starter 0 FTU | <50 | |
| 3C Starter 500FTU | 895 | 8% |
| 4D Starter 500 FTU | 790 | 13% |
| 5E Starter 0 FTU | <50 | |
| 6F Starter 0 FTU | <50 | |
| 7G Starter 500FTU | 456 | 13% |
| 8H Starter 500 FTU | 567 | 6% |
| 9I Starter 0 FTU | <50 | |
| 10J Starter 0 FTU | <50 | |
| 11K Starter 500FTU | 700 | 10% |
| 12L Starter 500 FTU | 737 | 4% |
| 1A Finisher 0 FTU | <50 | |
| 2B Finisher 0 FTU | <50 | |
| 3C Finisher 500FTU | 605 | 11% |
| 4D Finisher 500 FTU | 456 | 10% |
| 5E Finisher 0 FTU | <50 | |
| 6F Finisher 0 FTU | <50 | |
| 7G Finisher 500FTU | 474 | 6% |
| 8H Finisher 500 FTU | 728 | 9% |
| 9I Finisher 0 FTU | <50 | |

APPENDIX II-continued

| Sample information | Phytase activity (QB Elisa FTU/kg) | CV (%) |
|---|---|---|
| 10J Finisher 0 FTU | <50 | |
| 11K Finisher 500FTU | 713 | 2% |
| 12L Finisher 500 FTU | 560 | 10% |

The invention claimed is:

1. An animal feed including:
a nutrient component including one or more of a carbohydrate, fat and protein;
a phytase; and
betaine hydrochloride (BHCl),
wherein the phytase and BHCl are provided in the feed in a ratio of
about 0.5 to 5 g BHCl per kg of feed:750 to 5000 phytase unit (FTU) per kg of feed; and wherein the ratio of BHCl:phytase provide for an energy utilization that is greater than the sum of the energy utilization in a feed that includes phytase only or BHCl only.

2. The feed of claim 1, wherein the nutrient component of the feed has a starch content of not more than 270 g per kg of feed.

3. The feed of claim 1, wherein the protein content of the feed is from 150 to 250 g per kg of feed.

4. The feed of claim 1, wherein the fat content of the feed is not more than 45 g per kg of feed.

5. The feed of claim 1, wherein the feed is a poultry feed.

6. The animal feed of claim 1, wherein the phytase is of bacterial origin.

7. The animal feed of claim 6, wherein the phytase has an amino acid sequence of an *E. coli* phytase.

8. The animal feed of claim 1, wherein the BHCl and phytase are provided in a ratio of about 0.5 to 5 g BHCl per kg of feed:1000 to 3000 phytase unit (FTU) per kg of feed.

9. The animal feed of claim 1, wherein the nutrient component does not include the following micronutrients as an additive or synthetic component: methionine, choline, lysine, threonine and inorganic phosphate.

* * * * *